United States Patent [19]

Suzuki et al.

[11] Patent Number: 4,835,317

[45] Date of Patent: May 30, 1989

[54] 4-TERT.-BUTYL-1,2-BENZENEDITHIOL, COMPLEX COMPOUNDS DERIVED THEREFROM, AND A METHOD OF PRODUCING THE SAME

[75] Inventors: Michio Suzuki; Masao Kawamura; Kunioki Kato; Masahide Takahashi; Tsuyoshi Morishita; Kazuyuki Nakayama; Akio Nakatsuka, all of Hyogo, Japan

[73] Assignee: Seitetsu Kagaku Co., Ltd., Hyogo, Japan

[21] Appl. No.: 143,643

[22] Filed: Jan. 13, 1988

[30] Foreign Application Priority Data

Jan. 20, 1987 [JP]  Japan ................... 62-011928
Oct. 30, 1987 [JP]  Japan ................... 62-276584
Nov. 10, 1987 [JP]  Japan ................... 62-284884

[51] Int. Cl.$^4$ ............................... C07C 149/28
[52] U.S. Cl. ..................... 568/66; 556/113; 556/150
[58] Field of Search ............ 568/66, 68, 67; 356/54; 556/113, 146, 150

[56] References Cited

U.S. PATENT DOCUMENTS

4,555,497  11/1985  Coleman, III et al. ............... 556/54

FOREIGN PATENT DOCUMENTS

861573  2/1961  United Kingdom ................. 568/66

OTHER PUBLICATIONS

Sabat, et al. in *Anales De Quimica*, vol. 81, pp. 303–308 (1985).
*Chemical Abstracts*, Jul.–Dec. 1986, vol. 105.

*Primary Examiner*—Paul F. Shaver
*Assistant Examiner*—Stuart L. Hendrickson
*Attorney, Agent, or Firm*—Wenderoth, Lind & Ponack

[57] ABSTRACT

Novel compounds, 4-tert.-butyl-1,2-benzenedithiol and bis(4-tert.-butyl-1,2-dithiophenolate) metal complexes having the general formula of

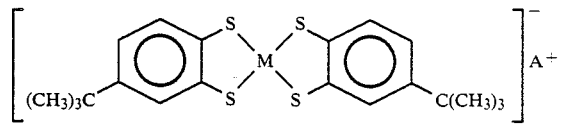

wherein M represents a trivalent transition metal, and A represents a quarternary ammonium are provided.

The novel benzenedithiol is produced by reacting 4-tert.-butylbenzenethiol or di(4-tert.-butylphenyl)disulfide with sulfur monochloride in the presence of iodine or a Lewis acid in a solvent, and then reducing the resultant product with a metal selected from the group consisting of zinc, tin, iron and aluminum in the presence of an acid.

The novel Cu, Co and Ni complexes are produced by reacting the benzenedithiol with a salt of the corresponding divalent transition metal in the presence of an alkoxide metal or a hydride metal and a quarternary ammonium salt in a solvent under an oxidative atmosphere.

The complexes strongly absorb rays in the region of ultraviolet, visible or near infrared, and are useful intermediates for the production of optical information recording media.

1 Claim, No Drawings

4-TERT.-BUTYL-1,2-BENZENEDITHIOL, COMPLEX COMPOUNDS DERIVED THEREFROM, AND A METHOD OF PRODUCING THE SAME

This invention relates to a novel compound, 4-tert.-butyl-1,2-benzenedithiol, complex compounds derived therefrom, and methods of producing these compounds.

It is already known that o-benzenedithiols such as 1,2-benzenedithiol, 4,5-dimethyl-1,2-benzenedithiol, 1,2,3,4-tetrachloro-5,6-benzenedithiol or 3,4,5,6-tetramethyl-1,2-benzenedithiol form benznedithiol-metal complexes with metal ions, and the complexes such as, for example, bis(1,2-dithiophenolate)nickel-tetra-n-butylammonium, strongly absorb light in the ultraviolet, visible or near infrared region, as described in J. Amer. Chem. Soc., 88, 43–50 and 4870–4875 (1966)). Therefore, the o-benzenedithiols are useful intermediates for the production of optical information recording media, as described in Japanese Patent Disclosure No. 57-11090 and No. 58-175693.

The present inventors have succeeded in producing a novel compound, 4-tert.-butyl-1,2-benzenedithiol, and found that this compound also forms metal complexes which absorb strongly ultraviolet, visible or near infrared rays, and are likewise useful for the production of optical information recording media.

It is, therefore, an object of the invention to provide a novel 4-tert.-butyl-1,2-benzenedithiol, and a method of producing the same.

It is also an object of the invention to provide a novel metal complexes of 4-tert.-butyl-1,2-benzenedithiol, and a method of producing the same.

According to the invention, there is provided a novel compound, 4-tert.-butyl-1,2-benzenedithiol, which is represented by

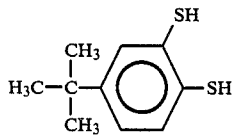

and liquid at normal temperatures.

This novel compound is produced by reacting 4-tert.-butylbenzenethiol represented by

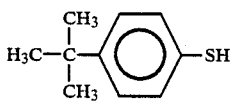

or di(4-tert.-butylphenyl)disulfide represented by

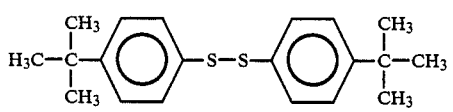

with sulfur monochloride in the presence of iodine or a Lewis acid in a solvent, and then redcuing the resultant product with a metal selected from the group consisting of zinc, tin, iron and aluminum in the presence of an acid.

In the first stage reaction, sulfur monochloride is used in amounts of about 0.5–2.0 moles, preferably of about 0.55–1.1 moles, per mole of 4-tert.-butylbenzenethiol, whereas in amounts of about 1–4 moles, preferably of about 1.1–2.2 moles, per mole of di(4-tert.-butylphenyl)-disulfide.

The reaction of the benzenethiol or the disulfide with sulfur monochloride is carried out in the presence of iodine or Lewis acids as a catalyst in a solvent under an ambient or air atmosphere. Iodine is used in amounts of about 0.1–4 moles, preferably of about 0.2–2 moles, per mole of the benzenethiol or the disulfide.

Lewis acids are also usable as a catalyst in the first stage reaction. Preferred Lewis acids usable in the invention include zinc halides such as zinc chloride, zinc bromide or zinc iodide, ferric halides such as ferric chloride, ferric bromide or ferric iodide, aluminum halides such as aluminum chloride, aluminum bromide or aluminum iodide, stannic halides such as stannic chloride, stannic bromide or stannic iodide, antimony halides such as antimony trichloride or antimony pentachloride, and boron trifluoride. Among these, zinc halides are preferred, and zinc chloride is most preferred.

The Lewis acids are used in amounts of about 0.05–2 moles, preferably of about 0.1–1 moles, per mole of 4-tert.-butylbenzenethiol, whereas in the range of about 0.1–4 moles, preferably of about 0.2–2 moles, per mole of di(4-tert.-butylphenyl)disulfide.

Further according to the invention, when 4-tert.-butylbenzenethiol is used as a starting material, a metal such as zinc, tin, iron or aluminum may be used in place of the Lewis acids, since the reaction of 4-tert.-butylbenzenethiol with sulfur monochloride produces hydrochloric acid which in turn reacts with the metals to in situ produce metal chlorides or Lewis acids in the reaction mixture.

Preferred solvents usable in the reaction include halogenated hydrocarbons such as chloroform, carbon tetrachloride, 1,2-dichloroethane, 1,1,2-trichloroethane, 1,1,2,2-tetrachloroethane, chlorobenzene, o-dichlorobenzene or 1,2,4-trichlorobenzene.

The reaction may be carried out at temperatures ranging from room temperatures to about 140° C., however, it is preferred that the reaction be carried out at room temperatures to about 40° C. when iodine is used as a catalyst, and at about 60°–100° C. when the Lewis acids are used. The reaction time depends upon the catalyst used, the amount thereof and the reaction temperatures, however, it is usually in the range of about 3–72 hours.

The second stage reduction reaction may be carried out successively in the same reaction vessel. However, the atmosphere is replaced by a nonoxidative atmosphere. Namely, after the first stage reaction, the atmosphere in the reaction vessel is replaced by a nonoxidative atmosphere, and then a metal and an acid are added to the resultant reaction mixture, and then the second stage reaction is started out under, for example, an inert gas atmosphere such a nitrogen, argon or helium atmosphere with stirring.

The metal is selected from the group consiting of zinc, tin, iron and aluminum, and is used preferably in the form of powders or granulates. The amount of the metal used is usually in the range of about 1–10 moles, preferably of about 3–7 moles, per mole of 4-tert.-butylbenzenethiol, whereas in the range of about 2–13 moles, preferably of about 4–11 moles, per mole of di(4-tert.-butylphenyl)disulfide.

The acid is used to keep the reaction mixture acidic during the reaction, and any acid is usable provided that it keeps the reaction mixture acidic during the reaction.

Preferred examples of the acids are inorganic acids such as hydrochloric acid or sulfuric acid. However, organic acids such as acetic acid are also usable. The acids are desirably used in amounts of at least an equivalent to the metal used, and usually in amounts of about one to two equivalents to the metal used.

It is preferred that the reaction mixture is kept at temperatures not more than room temperatures when the metal and the acid is added to the reaction mixture from the first stage reaction, and that the reaction is thereafter carried out at temperatures of about 40°–80° C. usually for about 0.5°–3 hours, although the reaction temperatures and times are not critical.

After the reaction, 4-tert.-butyl-1,2-benzenedithiol may be isolated fromt he reaction mixture by any conventional means such as extraction or distillation, or combination of these. Preferably the reaction mixture is extracted with chloroform, the chloroform is disstiled off from the solution, and then the resultant residuals are distilled under reduced pressures, to provide 4-tert.-butyl-1,2-benzenedithiol as a fraction.

The reaction mechanism is not yet clear, but it is assumed that 4-tert.-butylbenzenethiol reacts with sulfur monochloride in the first stage reaction to provide a polysulfide represented by

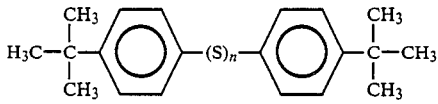

in which numerals of n are presumed not less than 2, and then the polysulfide further reacts with sulfur monochloride in the presence of iodine or the Lewis acid to undergo rearrangement, thereby providing, as an intermediate, a polysulfide, which has an average molecular weight of about 10,000 according to gel permeation chromatography and has presumably the following repeating unit of

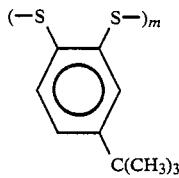

and this intermediate is presumably reduced to 4-tert.-butyl-1,2-benzenedithiol.

According to the invention, there is provided a bis(-4tert.-butyl-1,2-dithiophenolate)metal complex having the general formula of

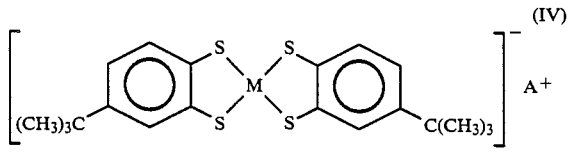

wherein M represents a trivalent transition metal, and A represents a quarternary ammonium.

The preferred transition metals in the complexes of the invention are group VIII and Ib metals of the periodic table which are capable of being trivalent ion state, and especially Co, Ni, Cu and Pt are most preferred.

The complexes of the invention are, therefore, advantageously obtained by use of divalent metal salts. By way of example, Co, Ni or Cu complexes are produced by reacting 4-tert.-butyl-1,2-benzenedithiol with the corresponding divalent metal salts in the presence of an metal alkoxide or metal hydride base and a quarternary ammonium salt in a solvent under an oxidative atmosphere such as an air atmosphere. The divalent transition metal salts usable are those that are soluble in the solvents used, and include halides such as chlorides, bromides or iodides, nitrates, sulfates or organic caboxylates such as acetates.

Therefore, divalent transition metal salts preferably usable are exemplified by halides such as cupric chloride, cupric bromide, cobaltous chloride, cobaltous bromide, cobaltous iodide, nickelous chloride, nickelous iodide or paladium chloride; nitrates such as cupric nitrate or cobaltous nitrate; sulfates such as cupric sulfate or cobaltous sulfate; acetates such as cupric acetate or cobaltous acetate.

However, tetravalent transition metal salts such as potassium chloroplatinate are also usable for the production of the complexes of the invention. When tetravalent transition metal salts are used, the complexes of the invention are obtained by reacting 4-tert.-butyl-1,2-benzenedithiol with a tetravalent transition metal salt in the presence of an metal alkoxide or a metal hydride base in a solvent under a nonoxidative atmosphere, and then carrying out a reaction of reducing the reaction product with a reducing agent in the presence of a quarternary ammonium salt in a nonoxidative or a reductive atmosphere. In this reduction reaction, a tetravalent metal is reduced to a trivalent state. Inert gas atmospheres such as a nitrogen, argon or helium atmosphere is preferred as the nonoxidative atmosphere.

The metal salts are used usually in amounts of about 0.4–10 moles per mole of 4-tert.-butyl-1,2-benzenedithiol. The use of smaller amounts than about 0.4 moles per mole of 4-tert.-butyl-1,2-benzenedithiol provides complexes in every small yields, whereas the use of too much amounts is undesirable from the economical standpoint.

The quarternary ammonium salts usable are tetraalkylammonium halides such tetra-n-butylammonium bromide, tetra-n-butylammonium chloride, tetraethylammonium bromide, tetraethylammonium chloride; tetraarylammonium halides such as tetraphenylammonium bromide, tetraphenylammonium chloride, tetrabenzylammonium chloride or tetrabenzylammonium bromide. Trialkylarylammonium halides such as trimethylbenzylammonium bromide, trimethylbenzylammonium chloride or tri-n-butylphenylammonium chloride; dialkyldiarylammonium halides such as di-n-butyldiphenylammonium bromide; or alkyltriarylammonium halides such as n-butyltriphenylammonium bromide are also usable as the quarternary ammonium salts in the reaction of the invention. It will be apparent that the quarternary ammonium groups A in the aforesaid general formula (IV) derive from these quarternary ammonium halides.

The quarternary ammonium salts are used in the reaction usually in amounts of about 0.4–1 moles per mole of 4-tert.-butyl-1,2-benzenedithiol.

The reaction is carried out in the presence of a base in a solvent. The bases usable in the reaction are those which are capable of converting thiol groups to metal salt forms. Therefore, the base preferably used are alkoxides or hydrides of alkali metals or alkaline earth metals, and are exemplified by sodium methoxide, potassium methoxide, sodium ethoxide, potassium ethoxide, potassium isopropoxide, potassium t-butoxide, sodium hydride, potassium hydride and calcium hydride. The bases are used usually in amounts of about 1.5–10 moles, preferably of about 2–5 moles, per mole of 4-tert.-butyl-1,2-benzenedithiol.

A variety of solvents are usable in the reaction, and preferred solvents include alcohols such as methanol, ethanol, isopropanol or tert.-butanol; halogenated hydrocarbons such as carbon tetrachloride, methylene chloride, chloroform, 1,1-dichloroethane, 1,2-dichloroethane, 1,1,2-trichloroethane, 1,1,1,2-tetrachloroethane, chlorobnzene, o-dichlobenzene or 1,2,4-trichlorobenzene; hydrocarbons such as benzene, toluene, xylene, hexane, heptane or octane; acid amides such as N,N,-dimethylformamide or N-methylpyrrolidone. However, most preferably sodium alkoxides such as sodium methoxide or ethoxide are used as bases and lower aliphatic alcohols of 1–4 carbons such as methanol, ethanol, isopropanol or tert.-butanol are used as solvents.

The reaction temperatures are usually room temperatures, and the reaction is carried out usually for about 0.25–5 hours under stirring.

By way of example, when 4-tert.-butyl-1,2-benzenedithiol is reacted with nickelous chloride in the presence of tetran-butylammonium bromide, the nickel-(II) is oxidized to nickel (III), and bis(4-tert.-butyl-1,2-dithiophenolate)nickel-tetran-butylammonium complex represented by

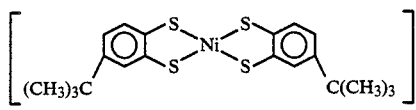

is obtained.

The invention will be more easily understood with reference to the following examples, which however are intended to illustrate the invention only, and are not to be construed as limiting the scope of the invention.

Example 1

An amount of 50 g of di(4-tert.-butylphenyl)disulfide, 8.5 g of iodine and 45 g of sulfur monochloride were dissolved in 340 g of chloroform, and the reaction was carried out at room temperatures for 24 hours. After the completion of the reaction, the atmosphere in the reaction vessel was replaced by a nitrogen atmosphere, and then 64 g of zinc powders were added to the resultant reaction mixture while cooling, and then 240 g of conc. hydrochloric acid.

After the reaction at 60° C. for one hour, the resultant reaction mixture was filtered and extracted with chloroform. The solvent was distilled off from the extract, and the residue was distilled under reduced pressures, to provide 4-tert.-butyl-1,2-benzenedithiol as a fraction of 125° C./4 mmHg in a yield of 68 %. The compound was found to have a purity of 99.3 %.

Boiling Point: 132°–133° C./5 mm Hg

| Elemental Analysis (for $C_{10}H_{14}S_2$): | | | |
|---|---|---|---|
| | C | H | S |
| Calculated: | 60.56 | 7.11 | 32.33 |
| Observed: | 60.66 | 7.12 | 32.23 |

NMR ($\delta$ ppm, CDCl$_3$): 7.0–7.4 (3H, m), 3.76 (1H, s), 3.61 (1H, s), 1.27 (9H, s).

IR ($\nu$max, NaCl, cm$^{-1}$): 2964, 2872, 2540, 1590, 1480, 1380, 1262, 1134, 1118, 1038, 816, 712, 600.

Example 2

An amount of 60 g of 4-tert.-butylbenzenethiol, 5.6 g of zinc chloride and 54 g of sulfur monochloride were dissolved in 400 g of 1,1,2,2-tetrachloroethane, and the reaction was carried out at 100° C. for 24 hours. After the completion of the reaction and cooling, the atmosphere in the reaction vessel was replaced by a nitrogen atmosphere, and 103 g of zinc powders and 327 g of conc. hydrochloric acid were added to the reaction mixture while keeping the temperatures of the mixture below 20° C., and then the reaction was carried out at 60° C. for two hours.

After working in the same manner as in Example 1, there were obtained 41 g of 4-tert.-butyl-1,2-benzenedithiol in a yield of 56 %.

Boiling Point: 132°–133° C./5 mm Hg

| Elemental Analysis (for $C_{10}H_{14}S_2$): | | | |
|---|---|---|---|
| | C | H | S |
| Calculated: | 60.56 | 7.11 | 32.33 |
| Observed: | 60.58 | 7.14 | 32.28 |

NMR ($\delta$ ppm, CDCl$_3$): 7.0–7.4 (3H, m), 3.76 (1H, s), 3.61 (1H, s), 1.27 (9H, s).

IR ($\nu$max, NaCl, cm$^{-1}$): 2964, 2872, 2540, 1590, 1480, 1380, 1262, 1134, 1118, 1038, 816, 712, 600.

Example 3

An amount of 30 g of di(4-tert.-butylphenyl)disulfide, 2.8 g of zinc chloride and 13.5 g of sulfur monochloride were dissolved in 200 g of 1,1,2,2-tetrachloroethane, and the reaction was carried out at 100° C. for 24 hours. After the completion of the reaction and cooling, the atmosphere in the reaction vessel was replaced by a nitrogen atmosphere, and then 47.6 g of zinc powders and 168 g of conc. hydrochloric acid were added to the reaction mixture while keeping the temperatures of the mixture below 20° C., and then the reaction was carried out at 60° C. for two hours.

After working in the same manner as in Example 1, there were obtained 19 g of 4-tert.-butyl-1,2-benzenedithiol in a yield of 53 %.

Example 4

An amount of 30 g of di(4-tert.-butylphenyl)disulfide, 2.8 g of zinc chloride and 13.5 g of sulfur monochloride were dissolved in 200 g of 1,1,2,2-tetrachloroethane, and the reaction was carried out at 100° C. for 24 hours. After the completion of the reaction and cooling, the atmosphere in the reaction vessel was replaced by a nitrogen atmosphere, and then 40.6 g of iron powders and 161 g of 50 % by weight sulfuric acid were added to the reaction mixture while keeping the temperatures of the mixture below 20° C., and then the reaction was carried out at 60° C. for two hours.

After the same procedures as in Example 1, there were obtained 18 g of 4-tert.-butyl-1,2-benzenedithiol in a yield of 50 %.

Examples 5–7

An amount of 14 g of 4-tert.-butylbenzene thiol was reacted with 12.5 g of sulfur monochloride in 40 g of chloroform in the presence of zinc iodide, ferric chloride and aluminum chloride, respectively, as a catalyst at temperatures for periods of time as shown in Table 1. After cooling, the atmosphere in the reaction vessel was replaced by a nitrogen atmosphere, and then 24 g of zinc powders and 75 g of conc. hydrochloric acid were added to the reaction mixture while keeping the temperatures of the mixture below 20° C., and then the reaction was carried out at 60° C. for two hours.

Then after working in the same manner as in Example 1, there were obtained 4-tert.-butyl-1,2-benzenedithiol in yields shown in Table 1.

TABLE 1

| Example | Catalyst | (Amount, g) | Temp. (°C.) | Time (hr) | Yield (%) |
|---|---|---|---|---|---|
| 5 | $ZnI_2$ | (3.0) | 60 | 24 | 60 |
| 6 | $FeCl_3$ | (1.4) | 20 | 36 | 32 |
| 7 | $AlCl_3$ | (1.2) | 20 | 40 | 40 |

Example 8

An amount of 14 g of 4-tert.-butylbenzenethiol, 0.6 g of zinc powder and 12.5 g of sulfur monochloride were dissolved in 40 g of 1,2-dichloroethane, and the reaction was carried out at 83° C. for 24 hours. After cooling the reaction mixture, the atmosphere in the reaction vessel was replaced by a nitrogen atmosphere, and then 72 g of tin granulates and 150 g of conc. hydrochloric acid were added to the resultant reaction mixture while keeping the temperatures of the mixture below 20° C., and then the reaction was carried out at 60° C. for two hours.

After the same procedures as in Example 1, there were obtained 13 g of 4-tert.-butyl-1,2-benzenedithiol with a purity of 99.5 % in a yield of 78 %. Boiling Point: 132°-133° C./5 mm Hg

| Elemental Analysis (for $C_{10}H_{14}S_2$): | | | |
|---|---|---|---|
| | C | H | S |
| Calculated: | 60.56 | 7.11 | 32.33 |
| Observed: | 60.60 | 7.10 | 32.30 |

NMR (δppm, $CDCl_3$): 7.0–7.4 (3H, m), 3.76 (1H, s), 3.61 (1H, s), 1.27 (9H, s).

IR ($\nu$max, NaCl, $cm^{-1}$): 2964, 2872, 2540, 1590, 1480, 1380, 1262, 1134, 1118, 1038, 816, 712, 600.

Example 9

An amount of 14 g of 4-tert.-butylbenzenethiol, 0.5 g of iron powders and 12.5 g of sulfur monochloride were dissolved in 40 g of chloroform, and the reaction was carried out at 60° C. for 5 hours. After cooling the reaction mixture, the atmosphere in the reaction vessel was replaced by a nitrogen atmosphere, and then 72 g of tin granulates and 150 g of conc. hydrochloric acid were added to the reaction mixture while keeping the temperatures of the mixture below 20° C., and then the reaction was carried out at 60° C. for five hours.

After working in the same manner as in Example 1, there were obtained 5.3 g of 4-tert.-butyl-1,2-benzenedithiol in a yield of 32 %.

Example 10

An amount of 0.2 g of aluminum powders was used in place of iron powders in the first stage reaction, and the reaction was carried out otherwise in the same manner as in Example 9, to provide 3.4 g of 4-tert.-butyl-1,2-benzenedithiol in a yield of 20 %.

Example 11

An amount of 5.0 g of 4-tert.-butyl-1,2-benzenedithiol was added to 64 g of a 4.7 % methanol solution of sodium methoxide and stirred. Then there were added thereto a solution of 2.2 g of cupric chloride dihydrate in 31 g of methanol, and then a solutin of 4.4 g of tetra-n-butylammonium bromide in 19 g of methanol, followed by stirring under an air atmosphere at room temperatures for one hour.

The resultant solids were filtered, recrystallized twice from methylene chloride/ethanol (1/5) and dried, to provide 5.9 g of bis(4-tert.-butyl-1,2-dithiophenolate)copper-tetra-n-butylammonium bromide complex as green solids in a yield of 68 %.

Melting Point: 169.5°–171.0° C.

| Elemental Analysis (for $C_{36}H_{60}S_4NCu$) | | | | | |
|---|---|---|---|---|---|
| | C | H | N | S | Cu |
| Calculated: | 61.88 | 8.66 | 2.00 | 18.36 | 9.10 |
| Observed: | 61.98 | 8.74 | 1.93 | 18.21 | 9.14 |

UV and Visible Spectra (methylene chloride): Maximum absorption wavelength: 323 nm, 398 nm, 645 nm. Molar absorption coefficient: 10200, 29800, 460

IR ($\nu$max, KBr, $cm^{-1}$): 2960, 2872, 1536, 1456, 1378, 1278, 1246, 1152, 1124, 862, 806, 736, 686, 604.

Example 12

An amount of 3.0 g of cobaltous chloride hexahydrate was used in place of cupric chloride dihydrate, and the reaction was carried out otherwise in the same manner as in Example 11

After the reaction, the resultant solids were filtered, recrystallized twice from methylene chloride/ethanol (1/5) and dried, to provide 5.8 g of bis(4-tert.-butyl-1,2-dithiophenolate)cobalt-tetra-n-butylammonium complex as blue solids in a yield of 66 %.

Melting Point: 167.5°–168.5° C.

| Elemental Analysis (for $C_{36}H_{60}S_4NCo$) | | | | | |
|---|---|---|---|---|---|
| | C | H | N | S | Co |
| Calculated: | 62.30 | 8.71 | 2.02 | 18.48 | 8.49 |
| Observed: | 62.40 | 8.81 | 2.12 | 18.17 | 8.50 |

UV and Visible Specra (methylene chloride): Maximum absorption wavelength: 317 nm, 361 nm, 666 nm. Molar absorption coefficient: 15100, 15900, 13200.

IR ($\nu$max, KBr, $cm^{-1}$): 2960, 2872, 1454, 1378, 1272, 1246, 1154, 1110, 878, 810, 686, 608.

Example 13

An amount of 5.0 g of 4-tert.-butyl-1,2-benzenedithiol was added to 64 g of a 4.7 % methanol solution of sodium methoxide and stirred. Then there were added thereto a solution of 3.1 g of nickel chloride hexahydrate in 31 g of methanol, and then 4.4 g of a solution of tetra-n-butylammonium bromide in 19 g of methanol were added and stirred under an air atmosphere at room temperatures for one hour.

After the completion of the reaction, the resultant solids were filtered, recrystallized twice from methylene chloride/ethanol (1/5), and dried, to provide 5.5 g of bis(r-tert.-butyl-1,2-dithiophenolate)nickel-tetra-n- butyl ammonium complex as blue solids in a yield of 63 %. Melting Point: 169°–170° C.

| Elemental Analysis (for $C_{36}H_{60}S_4NNi$) | | | | | |
| --- | --- | --- | --- | --- | --- |
| | C | H | N | S | Ni |
| Calculated: | 62.32 | 8.72 | 2.02 | 18.48 | 8.46 |
| Observed: | 62.41 | 8.78 | 1.96 | 18.49 | 8.36 |

UV, Visible and Near IR Spectra (methylene chloride): Maximum absorption wavelength: 313 nm, 360 nm, 924 nm. Molar absorption coefficient: 29860, 12000, 13080

IR ($\nu$max, KBr, cm$^{-1}$): 2964, 2872, 1576, 1480, 1376, 1294, 1242, 1092, 874, 806, 606.

Example 14

An amount of 5.0 g of 4-tert.-butyl-1,2-benzenedithiol was added to 55 g of a 5.0 % ethanol solution of sodium ethoxide under a nitrogen atmosphere and stirred. Then there were added thereto a solution of 5.3 g of potassium chloroplatinate in 31 g of ethanol, stirred for one hour, followed by the addition of 1.5 g of sodium borohydride and vigorous stirring for one hour under a nitrogen atmosphere. Finally 4.4 g of a solution of tetra-n-butylammonium bromide in 20 g of ethanol were added and stirred for one hour.

After the completion of the reaction, the resultant solids were filtered, recrystallized twice from ethanol-pyridine, and dried, to provide 4.7 g of bis(4-tert.-butyl-1,2-dithiophenolate)platinum-tetra-n-butylammonium complex as green solids in a yield of 45 %.

Melting Point: 178.5°–179.5° C.

| Elemental Analysis (for $C_{36}H_{60}S_4NPt$) | | | | | |
| --- | --- | --- | --- | --- | --- |
| | C | H | N | S | Pt |
| Calculated: | 52.08 | 7.28 | 1.69 | 15.45 | 23.50 |
| Observed: | 52.01 | 7.25 | 1.61 | 15.68 | 23.45 |

Near IR Spectra (methylene chloride): Maximum absorption wavelength: 920 nm. Molar absorption coefficient: 18000.

IR ($\nu$max, KBr, cm$^{-1}$): 2960, 2872, 1565, 1450, 1372, 1278, 1245, 1152, 1134, 872, 780, 736, 686, 605.

What is claimed:
1. 4-Tert.-butyl-1,2-benzenedithiol.

* * * * *